(12) United States Patent
Akagane

(10) Patent No.: US 10,010,342 B2
(45) Date of Patent: Jul. 3, 2018

(54) ULTRASONIC PROBE AND ULTRASONIC TREATMENT APPARATUS

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 4 days.

(21) Appl. No.: 15/142,331

(22) Filed: Apr. 29, 2016

(65) Prior Publication Data

US 2016/0242806 A1 Aug. 25, 2016

Related U.S. Application Data

(63) Continuation of application No. PCT/JP2014/078927, filed on Oct. 30, 2014.

(30) Foreign Application Priority Data

Nov. 1, 2013 (JP) .................................. 2013-228791

(51) Int. Cl.
*A61B 17/32* (2006.01)
*A61B 18/00* (2006.01)
(Continued)

(52) U.S. Cl.
CPC ................ *A61B 17/320092* (2013.01); *A61B 17/320068* (2013.01); *A61B 2017/00389* (2013.01);
(Continued)

(58) Field of Classification Search
CPC .... A61B 17/320092; A61B 17/320068; A61B 2017/320096; A61B 2017/00389;
(Continued)

(56) References Cited

U.S. PATENT DOCUMENTS 6,283,981 B1 9/2001 Beaupre
2005/0234484 A1 10/2005 Houser et al.
(Continued)

FOREIGN PATENT DOCUMENTS

EP 0 968 684 A1 1/2000
JP 2000-070279 A 3/2000
(Continued)

OTHER PUBLICATIONS

May 3, 2016 International Preliminary Report on Patentability issued in International Patent Application No. PCT/JP2014/078927.
(Continued)

*Primary Examiner* — Tuan V Nguyen
*Assistant Examiner* — Chima Igboko
(74) *Attorney, Agent, or Firm* — Oliff PLC

(57) ABSTRACT

In an ultrasonic probe, a curved portion gravity center of a probe curved portion located on a first perpendicular direction side with respect to a longitudinal axis. A boundary position between a probe relay portion and a probe main body portion is located on a distal side with respect to a reference antinode position which is located most distally among antinode positions of a longitudinal vibration located on a proximal direction side with respect to the probe curved portion. By a cross-section changing portion located at the boundary position, a cross section gravity center in a cross section of the probe relay portion perpendicular to the longitudinal axis is away from the longitudinal axis toward a second perpendicular direction opposite to the first perpendicular direction.

12 Claims, 13 Drawing Sheets

(51) Int. Cl.
    *A61B 18/14*    (2006.01)
    *A61B 17/28*    (2006.01)
    *A61B 17/29*    (2006.01)
    *A61B 17/00*    (2006.01)

(52) U.S. Cl.
    CPC .................. *A61B 2017/2825* (2013.01); *A61B 2017/2945* (2013.01); *A61B 2017/320072* (2013.01); *A61B 2017/320098* (2017.08); *A61B 2018/00607* (2013.01); *A61B 2018/1462* (2013.01)

(58) Field of Classification Search
    CPC .... A61B 2017/2945; A61B 2017/2825; A61B 2017/320072; A61B 2018/1462; A61B 2018/00607
    See application file for complete search history.

(56) References Cited

U.S. PATENT DOCUMENTS

| | | | |
|---|---|---|---|
| 2009/0216228 A1 | 8/2009 | Masuda | |
| 2009/0270891 A1* | 10/2009 | Beaupre | A61B 17/320092 606/169 |
| 2010/0106173 A1 | 4/2010 | Yoshimine | |

FOREIGN PATENT DOCUMENTS

| | | |
|---|---|---|
| JP | 2007-531563 A | 11/2007 |
| JP | 2009-160404 A | 7/2009 |
| JP | 2011-500161 A | 10/2011 |
| WO | 2014/024550 A1 | 2/2014 |
| WO | 2014/196640 A1 | 12/2014 |

OTHER PUBLICATIONS

Jan. 27, 2015 Search Report issued in International Patent Application No. PCT/JP2014/078927.
Oct. 13, 2015 Office Action issued in Japanese Patent Application No. 2015-537864.
Jan. 19, 2016 Office Action issued in Japanese Patent Application No. 2015-537864.
Sep. 13, 2017 Office Action issued in Chinese Patent Application No. 201480059816.X.
Oct. 6, 2017 Search Report issued in European Patent Application No. 14858829.6.

* cited by examiner

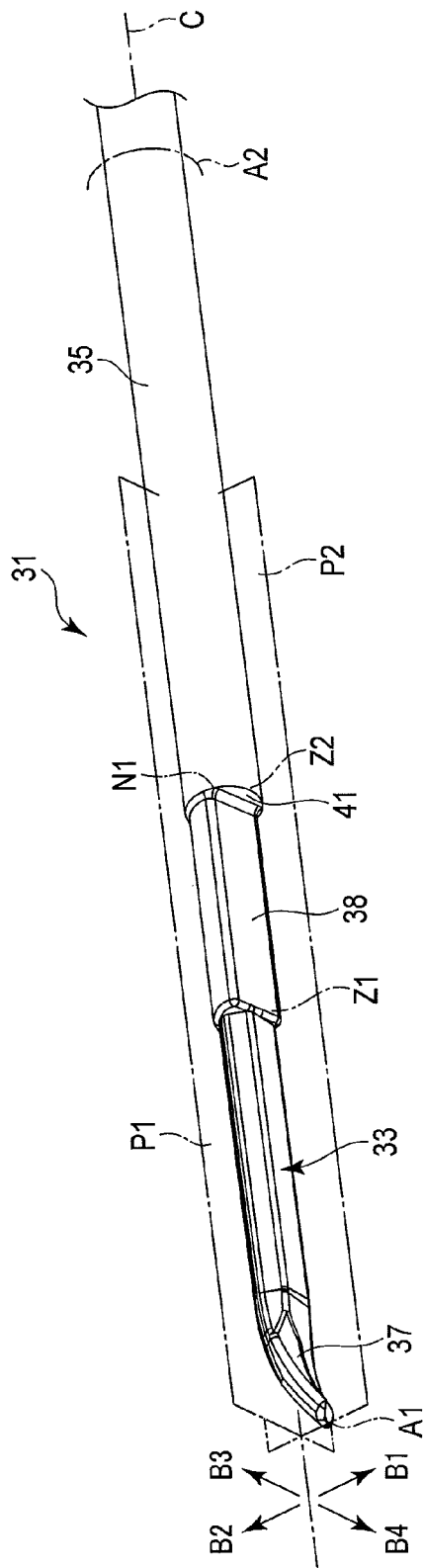
F I G. 4

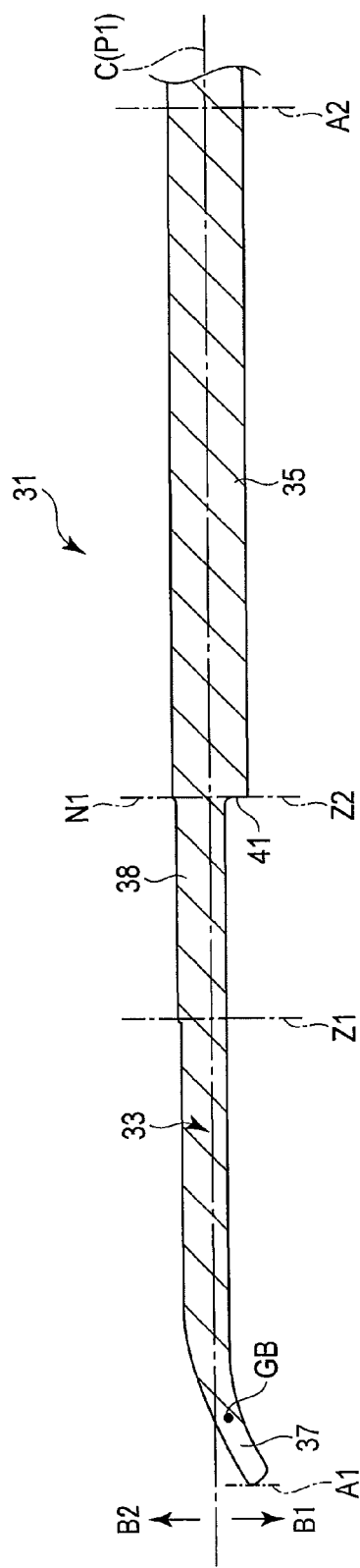
F I G. 5

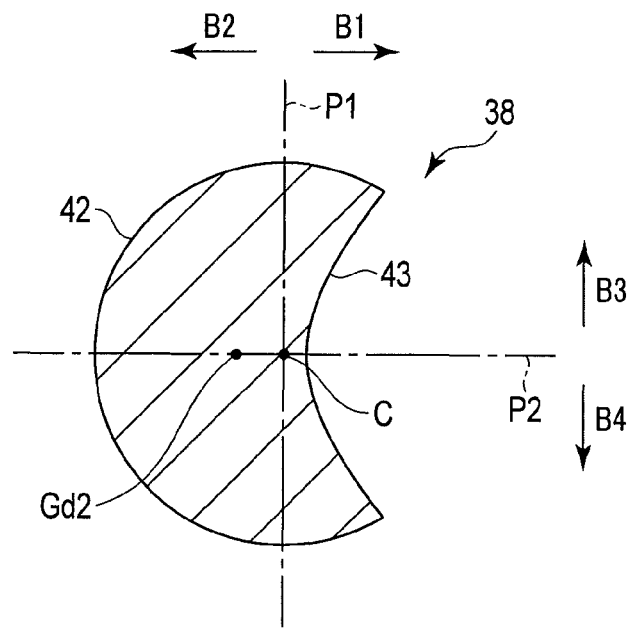
F I G. 9
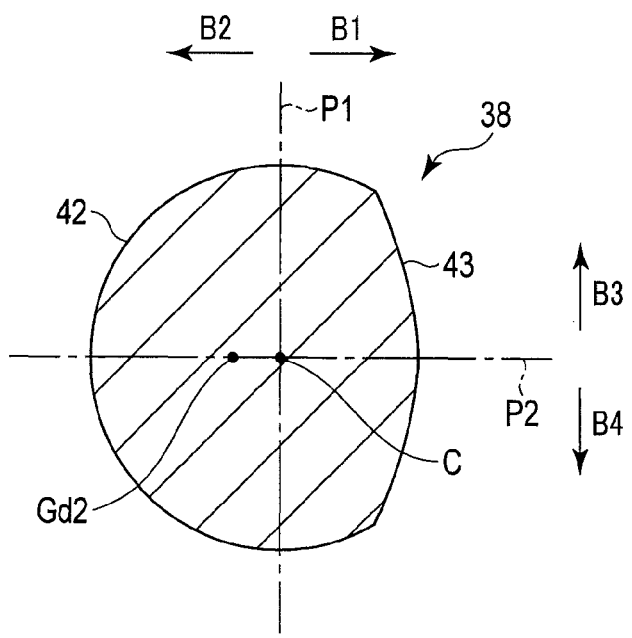
F I G. 10

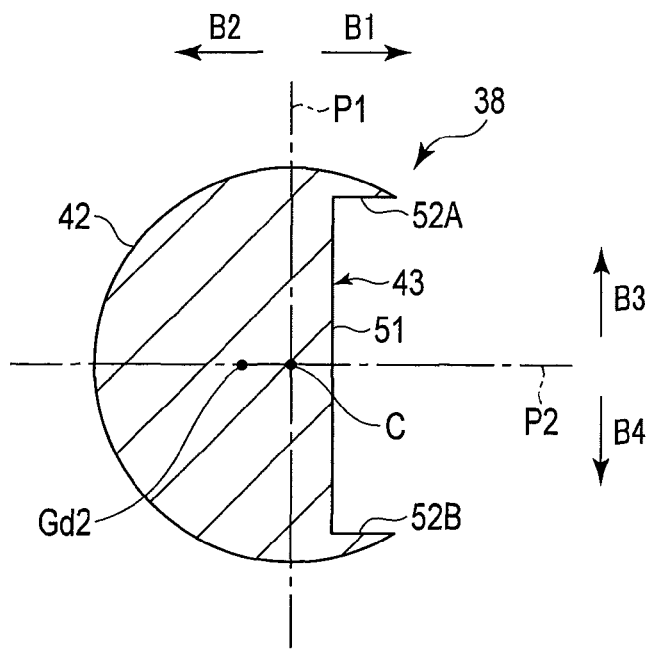
F I G. 11
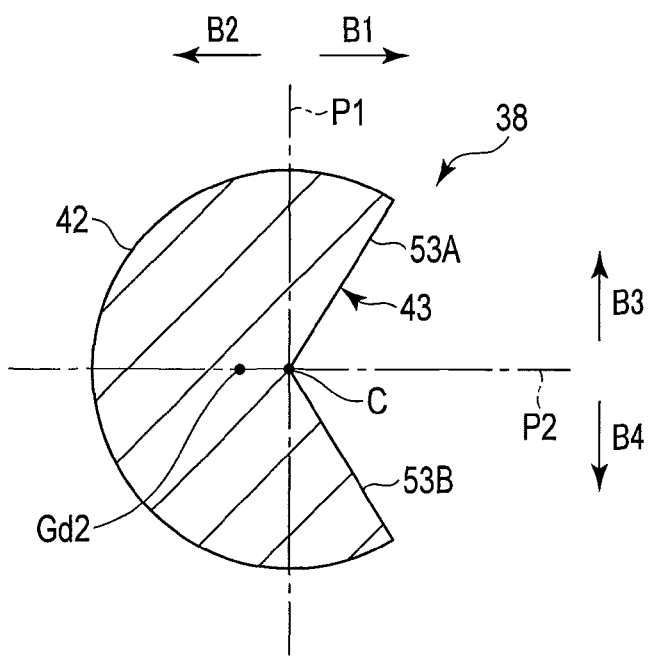
F I G. 12

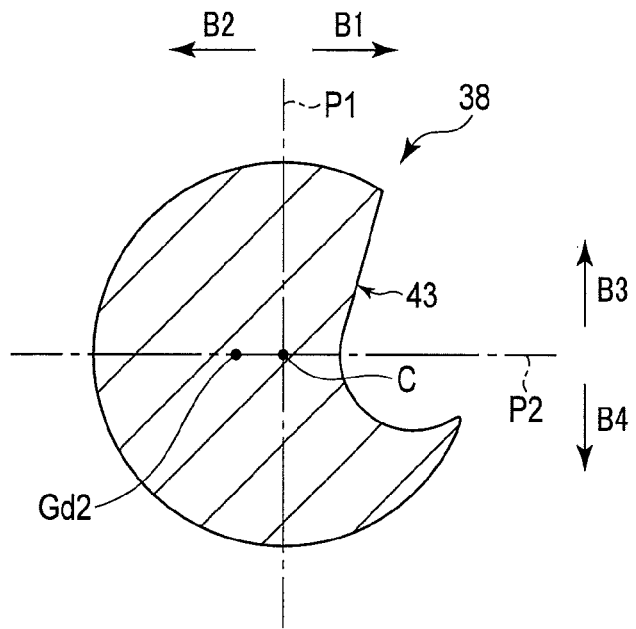
F I G. 13
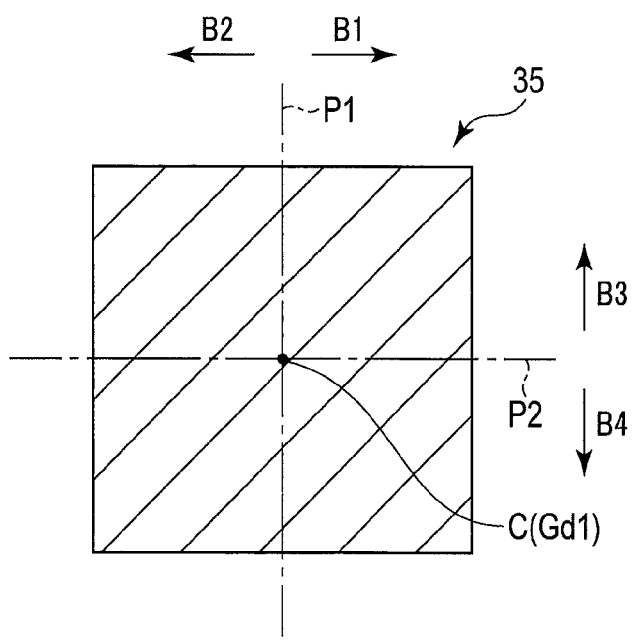
F I G. 14

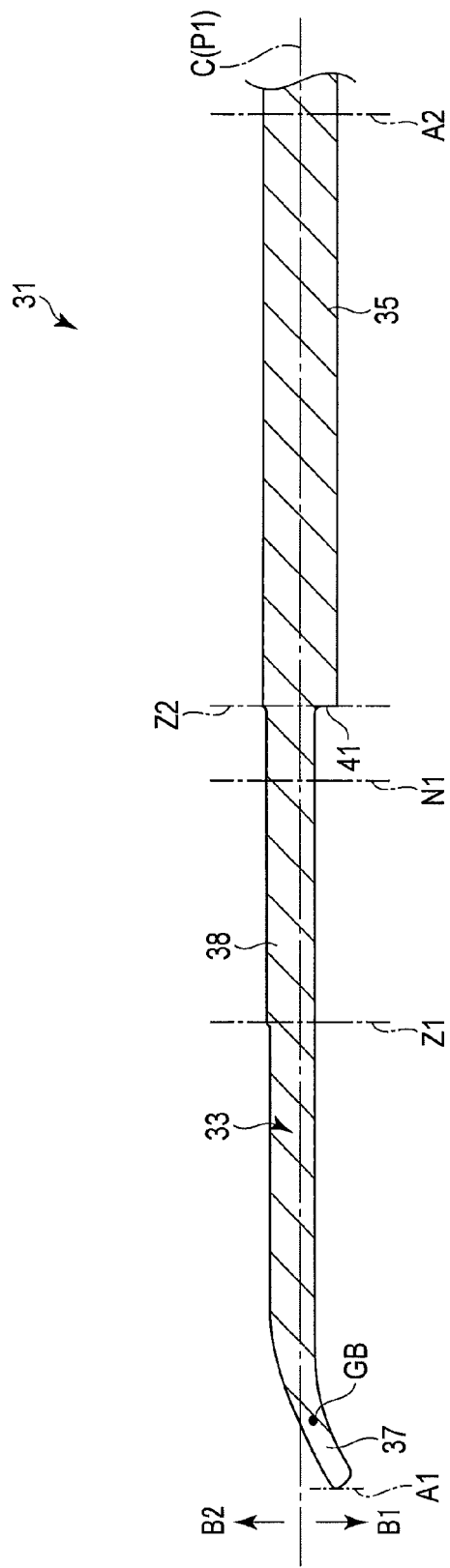
F I G. 16

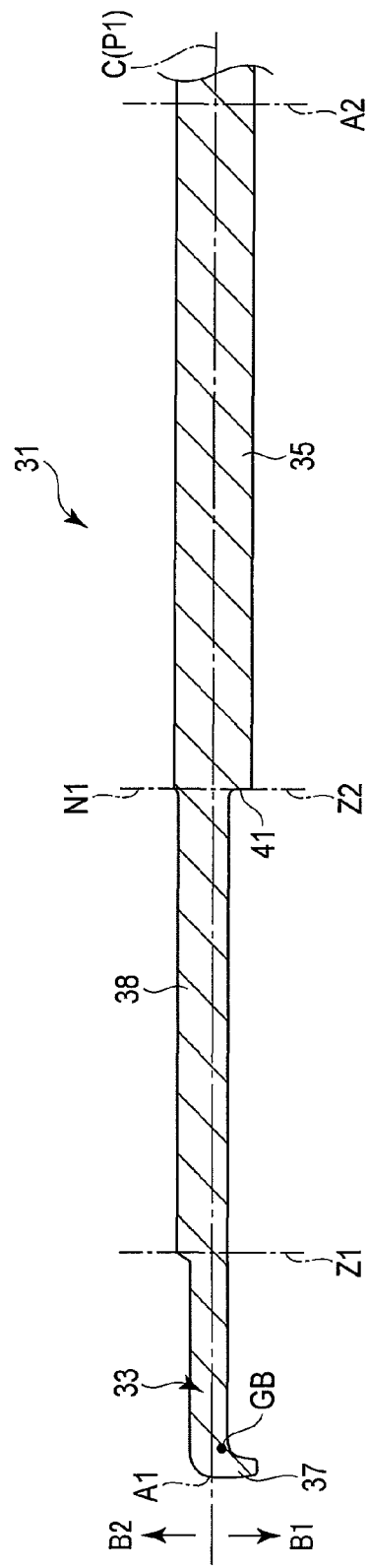
F I G. 18

ULTRASONIC PROBE AND ULTRASONIC TREATMENT APPARATUS

CROSS-REFERENCE TO RELATED APPLICATIONS

This is a Continuation application of PCT Application No. PCT/JP2014/078927, filed Oct. 30, 2014 and based upon and claiming the benefit of priority from prior Japanese Patent Application No. 2013-228791, filed Nov. 1, 2013, the entire contents of which are incorporated herein by reference.

BACKGROUND OF THE INVENTION

1. Field of the Invention

The present invention relates to an ultrasonic probe transmitting an ultrasonic vibration, and an ultrasonic treatment apparatus including the ultrasonic probe.

2. Description of the Related Art

Japanese Translation of PCT International Application No. 2011-500161 discloses an ultrasonic treatment apparatus including an ultrasonic probe configured to transmit an ultrasonic vibration from a proximal direction toward a distal direction. In the ultrasonic treatment apparatus, the ultrasonic probe includes a probe main body portion which extends along a longitudinal axis with the longitudinal axis serving as the axis center, and a distal treatment portion provided on the distal direction side with respect to the probe main body portion. The ultrasonic treatment apparatus is also provided with a jaw that is openable and closable relative to the distal treatment portion. In the ultrasonic probe, the ultrasonic vibration is transmitted to the distal treatment portion through the probe main body portion, and thereby a longitudinal vibration having a vibrating direction parallel to the longitudinal axis is generated. Using the longitudinal vibration, a treated object such as a living tissue held between the jaw and the distal treatment portion is treated. One of directions perpendicular to the longitudinal axis and perpendicular to the opening and closing directions of the jaw is referred to as a first perpendicular direction. The distal treatment portion is provided with a probe curved portion that is curved from a straight state running along the longitudinal axis toward the first perpendicular direction with respect to the longitudinal axis. Providing the probe curved portion secures visibility for the operator during treatment, and facilitates arrival of the distal treatment portion in a position where the operator can hold the treated object. Specifically, providing the probe curved portion enables the operator to easily use the ultrasonic probe during treatment.

BRIEF SUMMARY OF THE INVENTION

According to one aspect of the invention, an ultrasonic probe having a longitudinal axis, and performing a longitudinal vibration with a vibrating direction parallel to the longitudinal axis in a state of transmitting an ultrasonic vibration from a proximal direction toward a distal direction, the ultrasonic probe including: a probe main body portion extending along the longitudinal axis with the longitudinal axis serving as an axis center; a distal treatment portion provided on a distal direction side with respect to the probe main body portion, and including a probe curved portion curved from a straight state running along the longitudinal axis toward a first perpendicular direction, that is a direction perpendicular to the longitudinal axis, with respect to the longitudinal axis, the probe curved portion having a curved portion gravity center located on a first perpendicular direction side with respect to the longitudinal axis; a probe relay portion being continuous along the longitudinal axis between the probe main body portion and the distal treatment portion in an axis parallel direction parallel to the longitudinal axis, the probe relay portion having a boundary position with the probe main body portion, the boundary position being located on the distal direction side with respect to a reference antinode position and at a position different from antinode positions of the longitudinal vibration, when the reference antinode position is an antinode position located most distally among the antinode positions of the longitudinal vibration located on a proximal direction side with respect to the probe curved portion; and a cross-section changing portion provided at the boundary position between the probe main body portion and the probe relay portion, and reducing, in comparison with a first cross-sectional area of a first cross-sectional shape serving as a cross section of the probe main body portion perpendicular to the longitudinal axis, a second cross-sectional area of a second cross-sectional shape serving as a cross section of the probe relay portion perpendicular to the longitudinal axis to be smaller, the cross-section changing portion having a cross section gravity center in the second cross-sectional shape of the probe relay portion, the cross section gravity center continuously located on a second perpendicular direction side with respect to the longitudinal axis due to change from the first cross-sectional shape to the second cross-sectional shape in the cross-section changing portion, when the second perpendicular direction is a direction opposite to the first perpendicular direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view schematically illustrating a structure of the ultrasonic probe according to the first embodiment.

FIG. 5 is a cross-sectional view schematically illustrating the structure of the ultrasonic probe according to the first embodiment, with a cross section perpendicular to opening and closing directions of the jaw.

FIG. 9 is a cross-sectional view schematically illustrating a second cross-sectional shape in a cross section of the probe relay portion perpendicular to the longitudinal axis of the ultrasonic probe according to a first modification.

FIG. 10 is a cross-sectional view schematically illustrating a second cross-sectional shape in a cross section of the probe relay portion perpendicular to the longitudinal axis of the ultrasonic probe according to a second modification.

FIG. 11 is a cross-sectional view schematically illustrating a second cross-sectional shape in a cross section of the probe relay portion perpendicular to the longitudinal axis of the ultrasonic probe according to a third modification.

FIG. 12 is a cross-sectional view schematically illustrating a second cross-sectional shape in a cross section of the probe relay portion perpendicular to the longitudinal axis of the ultrasonic probe according to a fourth modification.

FIG. 13 is a cross-sectional view schematically illustrating a second cross-sectional shape in a cross section of the probe relay portion perpendicular to the longitudinal axis of the ultrasonic probe according to a fifth modification.

FIG. 14 is a cross-sectional view schematically illustrating a first cross-sectional shape in a cross section of the probe main body portion perpendicular to the longitudinal axis of the ultrasonic probe according to a sixth modification.

FIG. 16 is a cross-sectional view schematically illustrating a structure of the ultrasonic probe according to a seventh modification, with a cross section perpendicular to the opening and closing directions of the jaw.

FIG. 18 is a cross-sectional view schematically illustrating the ultrasonic probe according to the eighth modification, with a cross section perpendicular to a third perpendicular direction and a fourth perpendicular direction.

DETAILED DESCRIPTION OF THE INVENTION

First Embodiment

A first embodiment of the present invention will be explained hereinafter with reference to FIG. 1 to FIG. 8.

Figure 1:
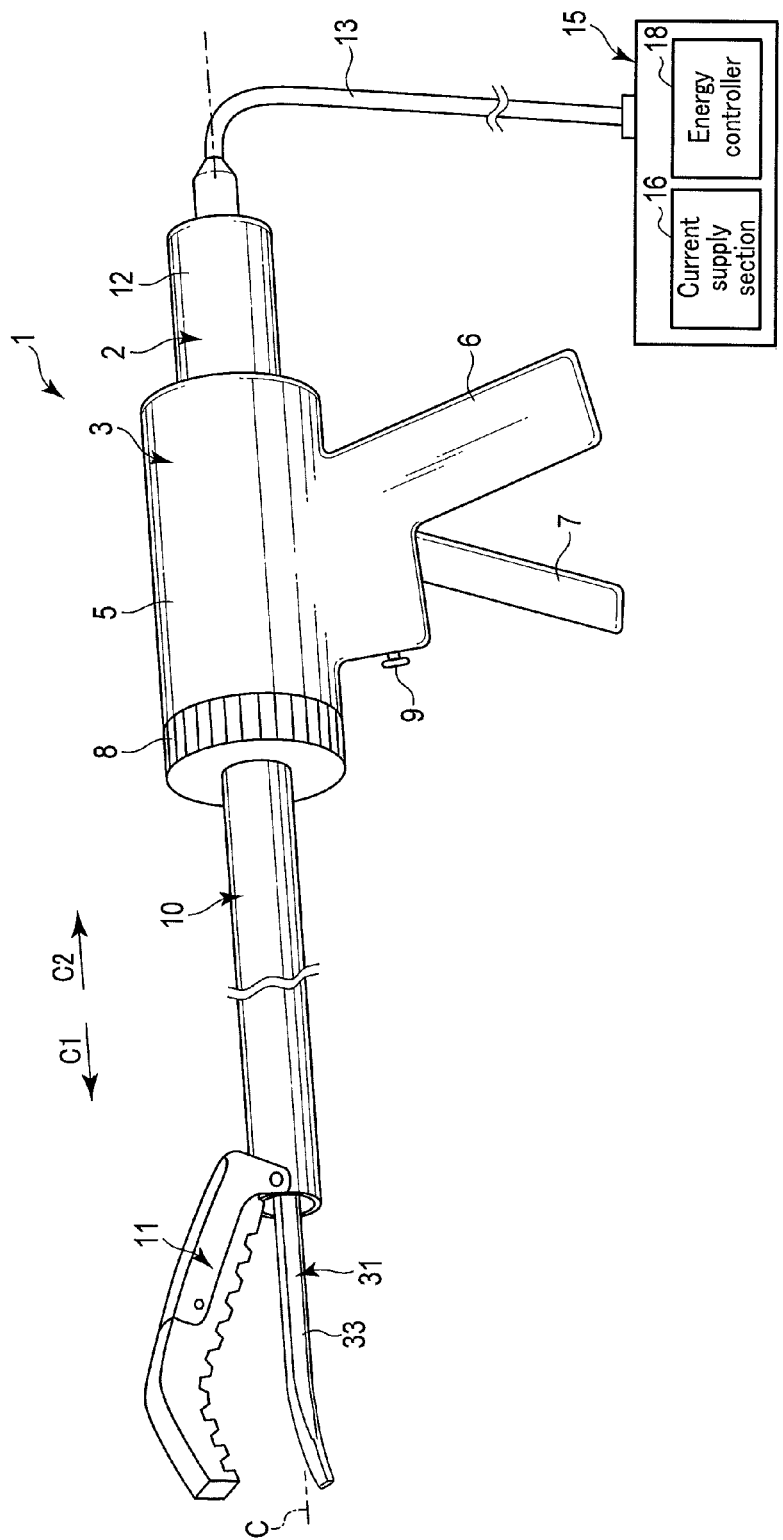
FIG. 1 is a schematic diagram illustrating a structure of an ultrasonic treatment apparatus according to a first embodiment.

FIG. 1 is a diagram illustrating a structure of an ultrasonic treatment apparatus 1 according to the present embodiment. As illustrated in FIG. 1, a longitudinal axis C runs through the ultrasonic treatment apparatus 1. One of directions parallel to the longitudinal axis C is a distal direction (direction of an arrow C1 in FIG. 1), and a direction opposite to the distal direction is a proximal direction (direction of an arrow C2 in FIG. 1). The distal direction and the proximal direction serve as an axis parallel direction parallel to the longitudinal axis C. In the present embodiment, the ultrasonic treatment apparatus 1 is an ultrasonic coagulation and incision treatment apparatus configured to perform treatment of incising a living tissue or the like simultaneously with coagulating the living tissue using ultrasonic vibration.

The ultrasonic treatment device 1 includes a transducer unit 2 and a holding unit 3. The holding unit 3 includes a cylindrical case 5 extending along the longitudinal axis C, a fixed handle 6 formed as one unitary piece with the cylindrical case 5, and a movable handle 7 rotatably attached to the cylindrical case 5. The movable handle 7 is rotated with a position attached to the cylindrical case 5 as the center, and thereby the movable handle 7 performs an opening movement or a closing movement relative to the fixed handle 6. The holding unit 3 also includes a rotating operating knob 8 attached to a distal direction side of the cylindrical case 5. The rotating operating knob 8 is rotatable with respect to the cylindrical case 5 with the longitudinal axis C serving as the center. An energy operation input button 9 serving as an energy operation input section is attached to the fixed handle 6.

The ultrasonic treatment apparatus 1 includes a sheath 10 extending along the longitudinal axis C. The sheath 10 is inserted into the rotating operating knob 8 and into the cylindrical case 5 from the distal direction side, and thereby the sheath 10 is attached to the holding unit 3. A jaw 11 is rotatably attached to a distal portion of the sheath 10. The movable handle 7 is connected to a movable cylindrical portion (not illustrated) of the sheath 10 inside the cylindrical case 5. A distal end of the movable cylindrical portion is connected to the jaw 11. By opening and closing the movable handle 7 with respect to the fixed handle 6, the movable cylindrical portion is moved along the longitudinal axis C. Thereby, the jaw 11 is rotated with the position attached to the sheath 10 as the center. The sheath 10 and the jaw 11 are rotatable together with the rotating operating knob 8, with the longitudinal axis C serving as the center, with respect to the cylindrical case 5.

The transducer unit 2 includes a transducer case 12 extending along the longitudinal axis C. The vibrator unit 2 is attached to the holding unit 3, by inserting the vibrator case 12 into the cylindrical case 5 from a proximal direction side. The transducer case 12 is coupled with the sheath 10 inside the cylindrical case 5. The transducer case 12 is rotatable together with the rotating operating knob 8 around the longitudinal axis C with respect to the cylindrical case 5. The transducer unit 2 is connected with one end of a cable 13. The other end of the cable 13 is connected to a control unit 15. The control unit 15 includes a current supply section 16 and an energy controller 18. The control unit 15 is, for example, an electric power supply device, and the current supply section 16 is formed of, for example, an electric power supply and an amplifier circuit provided in the electric power supply device. The energy controller 18 is formed of a CPU (Central Processing Unit) or an ASIC (Application Specific Integrated Unit), and a storage such as a memory.

Figure 2:
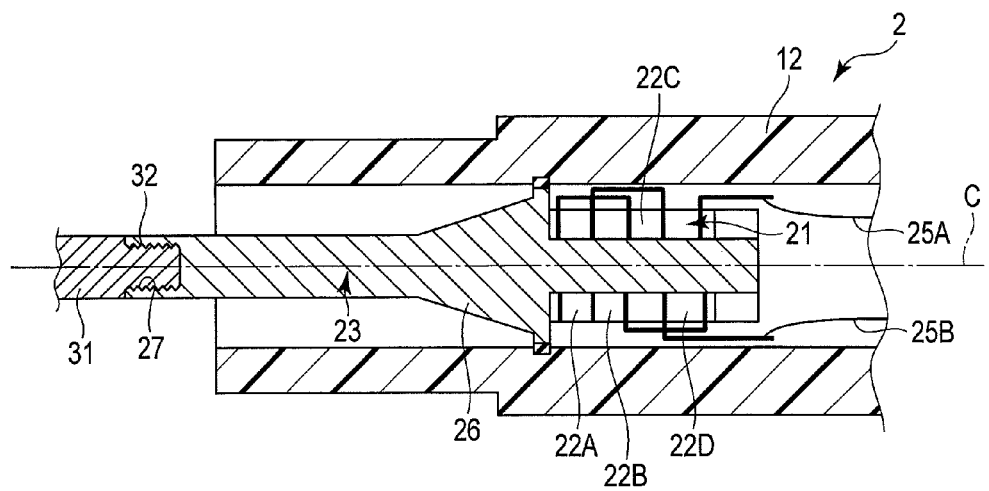
FIG. 2 is a cross-sectional view schematically illustrating a structure of a transducer unit according to the first embodiment.

FIG. 2 is a diagram illustrating a structure of the transducer unit 2. As illustrated in FIG. 2, the transducer unit 2 is provided with an ultrasonic transducer 21 serving as an ultrasonic generator configured to generate an ultrasonic vibration by supply of a current, inside the transducer case 12. The ultrasonic vibrator 21 includes a plurality of (four in the present embodiment) piezoelectric elements 22A to 22D, each of which converts a current into a vibration. The ultrasonic transducer 21 is attached to a horn member 23 extending along the longitudinal axis C. The ultrasonic vibration generated in the ultrasonic transducer 21 is transmitted to the horn member 23. A cross-sectional area changing portion 26 is formed in the horn member 23. In the cross-sectional area changing portion 26, a cross-sectional area perpendicular to the longitudinal axis C gradually decreases toward the distal direction. For this reason, the amplitude of the ultrasonic vibration is increased in the cross-sectional area changing portion 26. A distal portion of the horn member 23 is provided with a female screw portion 27.

An ultrasonic probe 31 is extends on a distal direction side of the horn member 23. In the present embodiment, the ultrasonic probe 31 is formed in a column shape (solid). The longitudinal axis C extends through the ultrasonic probe 31. A male screw portion 32 is provided in a proximal portion of the ultrasonic probe 31. The male screw portion 32 is screwed into the female screw portion 27, and thereby the ultrasonic probe 31 is connected with the distal direction side of the horn member 23. The horn member 23 extends up to the inside of the cylindrical case 5, and the ultrasonic probe 31 is connected with the horn member 23 inside the cylindrical case 5. The ultrasonic probe 31 extends from the inside of the cylindrical case 5 through the inside of the rotating operating knob 8 and the inside of the sheath 10. In addition, as illustrated in FIG. 1, the ultrasonic probe 31 is inserted through the sheath 10, in a state of projecting from the distal end of the sheath 10 toward the distal direction. The ultrasonic transducer 21, the horn member 23, and the ultrasonic probe 31 are rotatable together with the rotating operating knob 8 with respect to the cylindrical case 5, with the longitudinal axis C serving as the center.

The ultrasonic vibrator 21 is connected with one ends of electrical wires 25A and 25B. Each of the electrical wires 25A and 25B extends through the inside of the cable 13, and is connected at the other end thereof with the current supply section 16 of the control unit 15. By supplying current (alternating current) to the ultrasonic transducer 21 through the electrical wires 25A and 25B from the current supply section 16, the ultrasonic vibration is generated in the ultrasonic transducer 21 located on the proximal direction side with respect to the ultrasonic probe 31. The generated ultrasonic vibration is transmitted to the ultrasonic probe 31 through the horn member 23. In the ultrasonic probe 31, the ultrasonic vibration is transmitted from the proximal direction toward the distal direction. A longitudinal vibration having a vibrating direction parallel to the longitudinal axis C is generated, in a state where the ultrasonic vibration is transmitted in the ultrasonic probe 31. The proximal end of the horn member 23 (the proximal end of the ultrasonic transducer 21) and the distal end of the ultrasonic probe 31 serve as antinode positions of the longitudinal vibration.

The energy controller 18 controls a supply state of the current from the current supply section 16, based on an input of an energy operation with the energy operation input button 9. A switch (not illustrated) is provided inside the fixed handle 6. The switch is closed by pressing the energy operation input button 9 and inputting an energy operation. The switch is electrically connected to the energy controller 18. By closing the switch, an electrical signal is transmitted to the energy controller 18, and an input of the energy operation is detected. By detecting the input of the energy operation, a current is supplied from the current supply section 16 to the ultrasonic transducer 21, and the ultrasonic vibration is generated in the ultrasonic vibrator 21.

Figure 3:
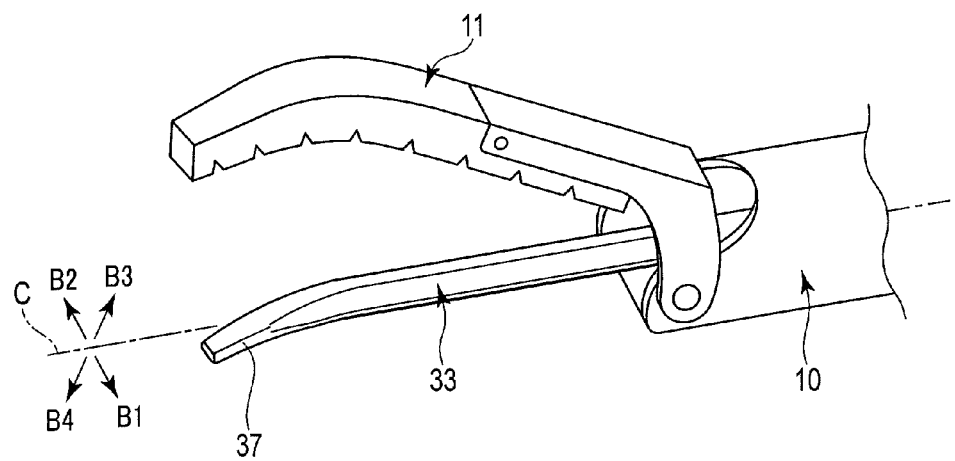
FIG. 3 is a perspective view schematically illustrating a structure of a distal portion of an ultrasonic probe, a distal portion of a sheath, and a jaw according to the first embodiment.

FIG. 3 is a diagram illustrating structures of the distal portion of the ultrasonic probe 31, the distal portion of the sheath 10, and the jaw 11. As illustrated in FIG. 3, the ultrasonic probe 31 includes a distal treatment portion 33 that projects from the distal end of the sheath 10 toward the distal direction. In the distal treatment portion 33, treatment of the treated object such as a living tissue is performed using the transmitted ultrasonic vibration. The jaw 11 is rotated with respect to the sheath 10, and thereby the jaw 11 is opened or closed with respect to the distal treatment portion 33. The opening and closing directions of the jaw 11 cross (are perpendicular to) the longitudinal axis C.

FIG. 4 and FIG. 5 are diagrams illustrating a structure of the ultrasonic probe 31. FIG. 4 is a perspective view thereof, and FIG. 5 is a cross-sectional view illustrating a cross section perpendicular to the opening and closing directions of the jaw 11. As illustrated in FIG. 3 to FIG. 5, the ultrasonic probe 31 includes a probe main body portion 35 that extends along the longitudinal axis C with the longitudinal axis C serving as the axis center. In the probe main body portion 35, the ultrasonic vibration is transmitted from the proximal direction toward the distal direction along the longitudinal axis C.

Suppose that one direction perpendicular to the longitudinal axis C serves as a first perpendicular direction (direction of an arrow B1 in FIG. 3 and FIG. 4), and a direction opposite to the first perpendicular direction serves as a second perpendicular direction (direction of an arrow B2 in FIG. 3 and FIG. 4). One of directions perpendicular to the longitudinal axis C and perpendicular to the first perpendicular direction and the second perpendicular direction serves as a third perpendicular direction (direction of an arrow B3 in FIG. 3 and FIG. 4), and a direction opposite to the third perpendicular direction serves as a fourth perpendicular direction (direction of an arrow B4 in FIG. 3 and FIG. 4). In the present embodiment, the first perpendicular direction and the second perpendicular direction are perpendicular to the opening and closing directions of the jaw 11, and the third perpendicular direction and the fourth perpendicular direction are parallel to the opening and closing directions of the jaw 11.

In addition, a first reference plane P1 is defined. The first reference plane P1 extends through the longitudinal axis C, and is perpendicular to the first perpendicular direction and the second perpendicular direction. A second reference plane P2 is also defined. The second reference plane P2 extends through the longitudinal axis C, and is perpendicular to the third perpendicular direction and the fourth perpendicular direction (that is, the opening and closing directions of the jaw 11). The probe main body portion 35 is plane-symmetrical with the first reference plane P1 serving as the center plane, and plane-symmetrical with the second reference plane P2 serving as the center plane. FIG. 5 illustrates a cross section obtained by cutting at the second reference plane P2.

In the ultrasonic probe 31, the distal treatment portion 33 is located on the distal direction side with respect to the probe main body portion 35. The distal treatment portion 33 is provided with a probe curved portion 37. The probe curved portion 37 is curved toward the first perpendicular direction with respect to the longitudinal axis C from a straight state extending along the longitudinal axis C. The probe curved portion 37 forms a distal end of the ultrasonic probe 31. Because the probe curved portion 37 is curved in the first perpendicular direction relative to the longitudinal axis C, the probe curved portion 37 is formed to be plane-asymmetrical with the first reference plane P1 as the center plane. In addition, a curved portion gravity center (center of gravity) GB of the probe curved portion 37 is disposed on the first perpendicular direction side with respect to the longitudinal axis C. The jaw 11 is also curved toward the first perpendicular direction in a position corresponding to the probe curved portion 37 of the distal treatment portion 33. The jaw 11 is curved in a shape corresponding to the probe curved portion 37.

A probe relay portion 38 continues between the probe main body portion 35 and the distal treatment portion 33 in the axis parallel direction that is parallel to the longitudinal axis C. The probe relay portion 38 extends along the longitudinal axis C. A first boundary position Z1 between the probe relay portion 38 and the distal treatment portion 33 serves as a distal end of the probe relay portion 38, and a second boundary position (boundary position) Z2 between the probe main body portion 35 and the probe relay portion 38 serves as a proximal end of the probe relay portion 38. The second boundary position Z2 is provided with a cross-section changing portion 41 in which a cross-sectional area of the ultrasonic probe 31 perpendicular to the longitudinal axis C is changed.

Figure 6:
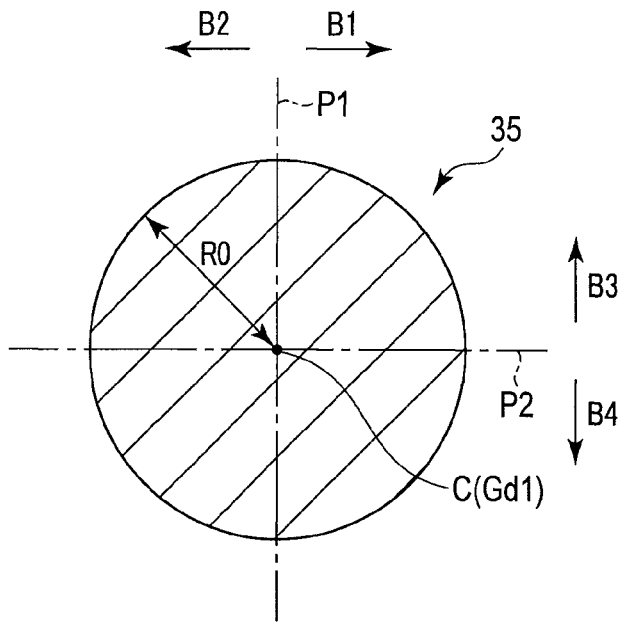
FIG. 6 is a cross-sectional view schematically illustrating a first cross-sectional shape in a cross section of a probe main body portion perpendicular to a longitudinal axis of the ultrasonic probe according to the first embodiment.
Figure 7:
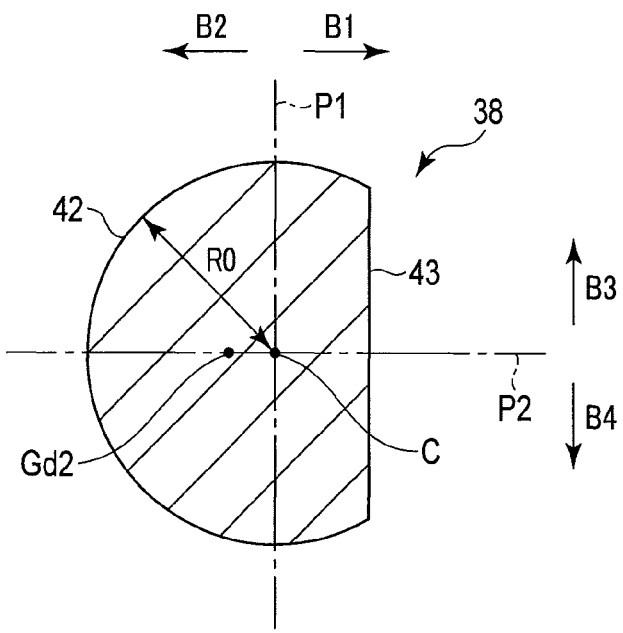
FIG. 7 is a cross-sectional view schematically illustrating a second cross-sectional shape in a cross section of a probe relay portion perpendicular to the longitudinal axis of the ultrasonic probe according to the first embodiment.

FIG. 6 is a diagram illustrating a first cross-sectional shape in a cross section of the probe main body portion 35 perpendicular to the longitudinal axis C, and FIG. 7 is a diagram illustrating a second cross-sectional shape in a cross section of the probe relay portion 38 perpendicular to the longitudinal axis C. As illustrated in FIG. 6, the first cross-sectional shape of the probe main body portion 35 is formed in a circular shape with the longitudinal axis C serving as the center. Accordingly, the first cross-sectional shape of the probe main body portion 35 is plane-symmetrical with the first reference plane P1 serving as the center plane, and plane-symmetrical with the second reference plane P2 serving as the center plane. For this reason, in the first cross-sectional shape, a cross section gravity center Gd1 of the probe main body portion 35 is located on the longitudinal axis C. The first cross-sectional shape has a radius serving as a reference size R0, and a first cross-sectional area S1.

As illustrated in FIG. 7, an arc curved surface 42 and a relay surface 43 form an outer circumferential surface of the second cross-sectional shape of the probe relay portion 38. The arc curved surface 42 is formed in an arc shape that is distant from the longitudinal axis C by the reference size R0 that is the same as the radius of the first cross-sectional shape. The relay surface 43 is formed in a plane shape, and disposed on the first perpendicular direction side (a side of a direction of an arrow B1 in FIG. 7) with respect to the longitudinal axis C. In the present embodiment, the relay surface 43 is parallel to the third perpendicular direction and the fourth perpendicular direction. A distance of relay surface 43 from the longitudinal axis C is smaller than the reference size R0. With the relay surface 43 provided as described above, the second cross-sectional shape of the probe relay portion 38 has a reduced cross-sectional area in a region on the first perpendicular direction side with respect to the longitudinal axis C, in comparison with the first cross-sectional shape of the probe main body portion 35. Accordingly, a second cross-sectional area S2 of the second cross-sectional shape is smaller than the first cross-sectional area S1 of the first cross-sectional shape.

With the relay surface 43 provided as described above, the second cross-sectional shape of the probe relay portion 38 is plane-asymmetrical with the first reference plane P1 serving as the center plane. In the second cross-sectional shape, a cross section gravity center Gd2 of the probe relay portion 38 is continuously disposed on the second perpendicular direction side with respect to the longitudinal axis C. However, the second cross-sectional shape is plane-symmetrical with the second reference plane P2 serving as the center plane. For this reason, in the second cross-sectional shape, the cross section gravity center Gd2 of the probe relay portion 38 is not shifted from the longitudinal axis C in the third perpendicular direction and the fourth perpendicular direction. Specifically, in the second cross-sectional shape, the cross section gravity center Gd2 of the probe relay portion 38 is disposed at a position substantially agreeing with the longitudinal axis C in the third perpendicular direction and the fourth perpendicular direction. The description "substantially agreeing" does not mean that the cross section gravity center Gd2 of the probe relay portion 38 is disposed at a position completely agreeing with the longitudinal axis C according to the third perpendicular direction and the fourth perpendicular direction. Specifically, a slight difference in position is allowed, as long as the cross section gravity center Gd2 of the probe relay portion 38 can be substantially regarded as not being shifted from the longitudinal axis C in the third perpendicular direction and the fourth perpendicular direction even with the difference.

As described above, the cross section gravity center Gd2 of the probe relay portion 38 in the second cross-sectional shape is shifted only toward the second perpendicular direction from the cross section gravity center Gd1 of the probe main body portion 35 in the first cross-sectional shape. Specifically, in the cross-section changing portion 41 provided in the second boundary position (boundary position) B2 between the probe main body portion 35 and the probe relay portion 38, the cross section gravity center (Gd1, Gd2) in the cross sections perpendicular to the longitudinal axis C is shifted only toward the second perpendicular direction.

As illustrated in FIG. 5, in the ultrasonic probe 31, the distal end (the distal end of the ultrasonic probe 31) of the probe curved portion 37 serves as an antinode position A1 of the longitudinal vibration. The antinode position A1 serves as a most distal antinode position located most distally most among antinode positions of the longitudinal vibration. In addition, in the present embodiment, the second boundary position Z2 between the probe main body portion 35 and the probe relay portion 38 is located at a node position N1 of the longitudinal vibration. Accordingly, the cross-section changing portion 41 is located at the node position (cross-section changing node position) N1 different from antinode positions of the longitudinal vibration.

An antinode position A2 located most distally among antinode positions of the longitudinal vibration that are located on the proximal direction side with respect to the probe curved portion 37 serves as a reference antinode position. The node position N1 serving as a cross-section changing node position is located between the antinode position (most distal antinode position) A1 and the antinode position (reference antinode position) A2. The node position N1 is also located between the antinode position A2 and the proximal end of the distal treatment portion 33 in the axis parallel direction parallel to the longitudinal axis C. With the structure as described above, the second boundary position Z2 between the probe relay portion 38 and the probe main body portion 35 is located on the distal direction side with respect to the antinode position (reference antinode position) A2. In addition, the node position N1 is the most distal node position located most distally among node positions of the longitudinal vibration. The ultrasonic probe 31 performs the longitudinal vibration at a predetermined frequency with which the antinode positions (A1, A2) and the node position (N1) described above are defined, by transmission of the ultrasonic vibration from the ultrasonic transducer 21 through the horn member 23. Specifically, the ultrasonic probe 31 is longitudinally vibrated at a predetermined frequency with which antinode positions including the antinode positions A1 and A2 and node positions including the node position N1 are located in respective predetermined positions in to the axis parallel direction.

In the ultrasonic treatment apparatus 1, the probe relay portion 38 is located inside the sheath 10. Accordingly, the antinode position (reference antinode position) A2 and the node position (cross-section changing node position) N1 are located inside the sheath 10.

The following is explanation of functions and effects of the ultrasonic treatment apparatus 1 and the ultrasonic probe 31 according to the present embodiment. When a treated object such as a living tissue is treated using the ultrasonic treatment apparatus 1, the jaw 11, the ultrasonic probe 31, and the sheath 10 are inserted into the body cavity. Thereafter, in a state where the jaw 11 is opened relative to the distal treatment portion 33, the distal treatment portion 33 is disposed in a position where the treated object can be held between the jaw 11 and the distal treatment portion 33. The distal treatment portion 33 is provided with the probe curved portion 37 that is curved toward the first perpendicular direction with respect to the longitudinal axis C. With this structure, the distal treatment portion 33 is easily caused to arrive in the position where the treated object can be held between the jaw 11 and the distal treatment portion 33.

Thereafter, the movable handle 7 is closed with respect to the fixed handle 6, in a state where the treated object is positioned between the jaw 11 and the distal treatment portion 33. In this manner, the jaw 11 is closed relative to the distal treatment portion 33, and the treated object is held between the jaw 11 and the distal treatment portion 33. With the probe curved portion 37 provided in the distal treatment portion 33, visibility for the operator is secured in treatment in which the treated object is held between the jaw 11 and the distal treatment portion 33.

The jaw 11 is curved toward the first perpendicular direction, in the position corresponding to the probe curved portion 37 of the distal treatment portion 33. The jaw 11 is also curved in a shape corresponding to the probe curved portion 37. This structure improves visibility for the surgeon in treatment in which the treated object is held between the jaw 11 and the distal treatment portion 33.

Thereafter, an energy input operation is performed by the energy operation input button 9, thereby a current is supplied from the current supply section 16 to the ultrasonic transducer 21, and the ultrasonic vibration is generated in the ultrasonic vibrator 21. The generated ultrasonic vibration is transmitted to the ultrasonic probe 31 through the horn member 23. In the ultrasonic probe 31, the ultrasonic vibration is transmitted to the distal treatment portion 33 from the proximal direction toward the distal direction, and the ultrasonic probe 31 performs the longitudinal vibration with the vibrating direction parallel to the longitudinal axis C. Frictional heat is generated between the distal treatment portion 33 and the treated object, by the longitudinal vibration of the distal treatment portion 33 in the state where the treated object is held between the jaw 11 and the distal treatment portion 33. By the frictional heat, the treated object is incised and coagulated simultaneously.

In addition to the treatment using the ultrasonic vibration described above, the ultrasonic treatment apparatus 1 may perform a treatment using a high-frequency current. In the treatment using a high-frequency current, the held treated object is treated with the jaw 11 and the distal treatment portion 33 serving as electrodes.

Figure 8:
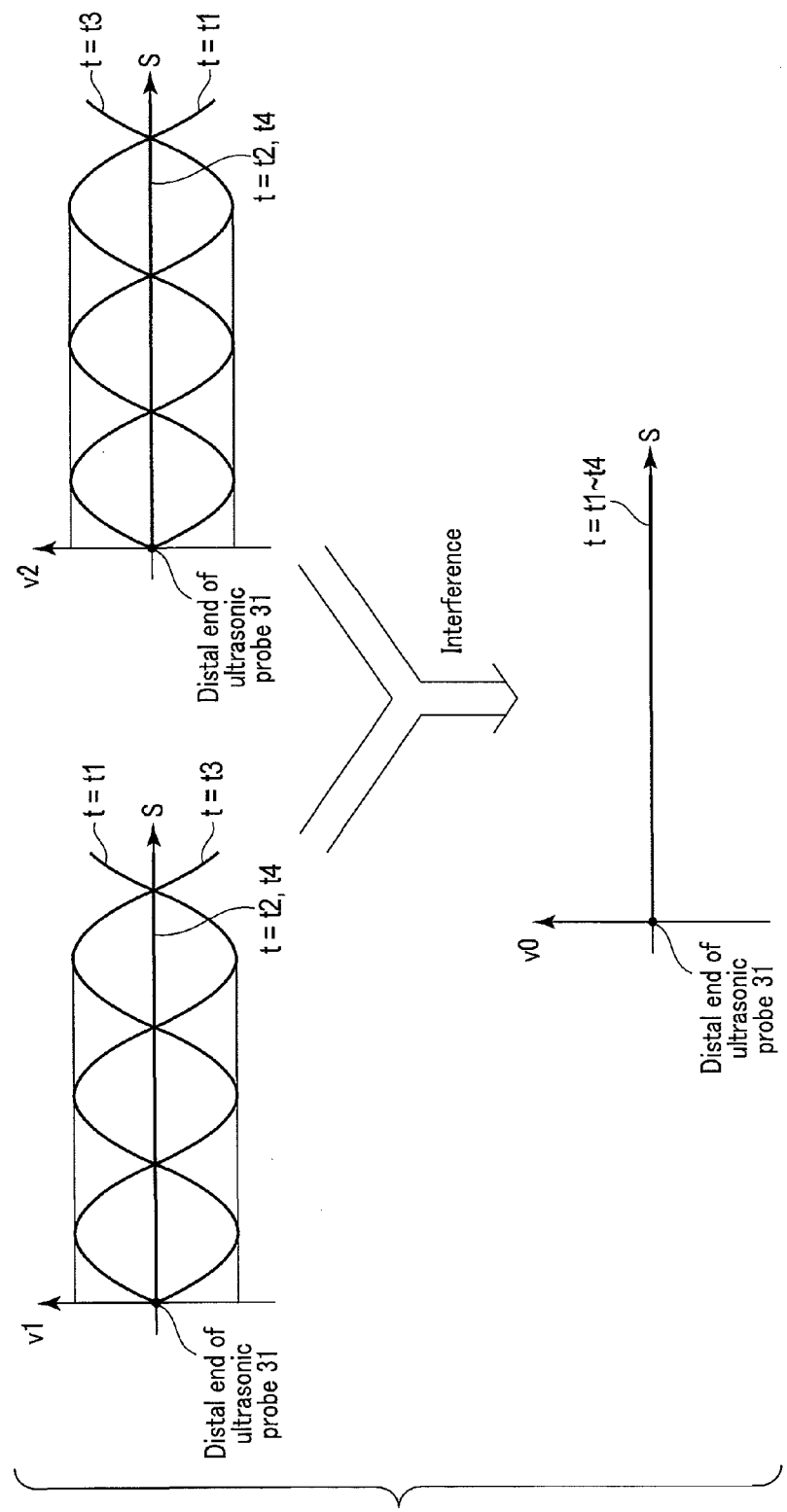
FIG. 8 is a schematic diagram illustrating an abnormal vibration generated separately from a longitudinal vibration in a state where the ultrasonic probe according to the first embodiment transmits an ultrasonic vibration.

FIG. 8 is a diagram illustrating an abnormal vibration generated separately from the longitudinal vibration in a state where the ultrasonic probe 31 transmits the ultrasonic vibration. The distal treatment portion 33 of the ultrasonic probe 31 is provided with the probe curved portion 37 in which a curved portion gravity center (center of gravity) GB is located on the first perpendicular direction side with respect to the longitudinal axis C. For this reason, as illustrated in FIG. 8, the ultrasonic vibration is transmitted to the probe relay portion 38 and the distal treatment portion 33 via the probe main body portion 35, and thereby a first transverse vibration (v1) is generated as the abnormal vibration, separately from the longitudinal vibration used for treatment. The first transverse vibration is generated due to the curvature of the probe curved portion 37, and has a vibrating direction parallel to the first perpendicular direction and the second perpendicular direction.

In the cross-section changing portion 41 provided in the second boundary position (boundary position) Z2, the cross section gravity center (Gd1, Gd2) in cross sections perpendicular to the longitudinal axis C changes. In the state where the ultrasonic probe 31 transmits the ultrasonic vibration, stress caused by the ultrasonic vibration is generated at a position different from the antinode positions (for example, A1 and A2) of longitudinal vibration. The node position N1 at which the cross-section changing portion 41 is located is a position different from antinode positions of longitudinal vibration, and stress caused by ultrasonic vibration is generated thereat. Accordingly, in the cross-section changing portion 41, the cross section gravity center (Gd1, Gd2) in cross sections perpendicular to the longitudinal axis C is shifted at a position at which stress due to the ultrasonic vibration acts. For this reason, as illustrated in FIG. 8, the ultrasonic vibration is transmitted to the probe relay portion 38 and the distal treatment portion 33 via the probe main body portion 35, and thereby a second transverse vibration (v2) is generated as the imprecise vibration, separately from the longitudinal vibration and the first transverse vibration.

FIG. 8 illustrates the first transverse vibration as v1, and illustrates the second transverse vibration as v2. In addition, FIG. 8 illustrates a state where the first transverse vibration (v1) interferes with the second transverse vibration (v2) as v0. FIG. 8 illustrates a distance toward the proximal direction from the distal end of the ultrasonic probe 31 as S. The reference symbol t denotes time, and the state (vibration state) is changed in the order of t1, t2, t3, t4, t1, t2, . . . .

The cross section gravity center Gd2 of the probe relay portion 38 is not shifted from the longitudinal axis C in the third perpendicular direction and the fourth perpendicular direction, but shifted from the longitudinal axis C only toward the second perpendicular direction. For this reason, the vibrating direction of the second transverse vibration is parallel with the first perpendicular direction and the second perpendicular direction, and agrees with that of the first transverse vibration. In addition, the frequency of the second transverse vibration is the same as the frequency of the first transverse vibration.

In addition, the antinode position (reference antinode position) A2 is an antinode position located most distally among antinode positions located on the proximal direction side with respect to the probe curved portion 37, and the node position N1 provided with the cross-section changing portion 41 is located on the distal direction side with respect to the antinode position A2. Specifically, in the ultrasonic probe 31, the cross section gravity center Gd2 of the probe relay portion 38 is shifted from the longitudinal axis C only toward the second perpendicular direction, in the cross-section changing portion 41 located on the distal direction side with respect to the antinode position A2. For this reason, the second transverse vibration is generated in a state where the first transverse vibration and the second transverse vibration cancel each other by interference.

As the first transverse vibration and the second transverse vibration cancel each other out by interference, the influence of the abnormal vibration such as the first transverse vibration and the second transverse vibration on the longitudinal vibration is reduced. Because the influence of the abnormal vibration is reduced, stability of the ultrasonic vibration is secured in the ultrasonic probe 31. Thereby, the ultrasonic vibration is properly transmitted in the ultrasonic probe 31, and treatment performance is secured in treatment using the ultrasonic vibration, such as in the treatment in which incision is performed simultaneously with coagulation as described above.

In addition, the node position N1 provided with the cross-section changing portion 41 is located between the antinode position (most distal antinode position) A1 and the antinode position (reference antinode position) A2 that is distant from the antinode position A1 toward the proximal direction by a half wavelength of the longitudinal vibration. Specifically, the cross-section changing portion 41 is located at the node position N1 located most distally among node positions of the ultrasonic vibration. Because the cross section gravity center Gd2 of the probe relay portion 38 is shifted from the longitudinal axis C toward the second perpendicular direction at the node position N1, the second transverse vibration has a phase opposite to the first transverse vibration. For this reason, by setting the amplitude of the first transverse vibration to be the same as the amplitude of the second transverse vibration, a state is obtained in which the first transverse vibration and the second transverse vibration are not substantially generated. This removes influence of the first transverse vibration and the second transverse vibration on the longitudinal vibration, and further reduces influence of the abnormal vibration on the longitudinal vibration. This structure further surely secures the stability of the ultrasonic vibration in the ultrasonic probe 31.

The amplitude of the second transverse vibration is changed in accordance with the distance of the cross section gravity center Gd2 of the probe relay portion 38 from the longitudinal axis C toward the second perpendicular direction. Accordingly, the amplitude of the second transverse vibration is changed in accordance with the second cross-sectional shape of the probe relay portion 38. For this reason, in the present embodiment in which the cross-section changing portion 41 is located at the node position N1 (the second transverse vibration has a phase opposite to the first transverse vibration), the second cross-sectional shape is preferably formed in a state where the first transverse vibration and the second transverse vibration have the same amplitude.

As described above, the present embodiment provides the ultrasonic probe 31 that can be easily used by the operator and secures stability of the ultrasonic vibration. The present embodiment also provides the ultrasonic treatment apparatus 1 including the ultrasonic probe 31.

(Modifications)

In the first embodiment, only the ultrasonic vibration is used as energy in treatment, but it is not limited thereto. For example, a high-frequency current may be used in treatment, in addition to the ultrasonic vibration. In this case, the energy controller 18 controls the supply state of the current that generates the ultrasonic vibration and is supplied from the current supply section 16 to the ultrasonic transducer 21, and also controls the output state of the high-frequency current from the control unit 15. With output of a high-frequency current from the control unit 15, conductive portions (not illustrated) of the distal treatment portion 33 and the jaw 11 function as electrodes. A high-frequency current is output to the distal treatment portion 33 and the jaw 11 in the state where the treated object is held between the distal treatment portion 33 and the jaw 11, and thereby the high-frequency current flows through the treated object. The high-frequency current renature the treated object, and improves coagulability of the treated object.

In the first embodiment, the relay surface 43 of the second cross-sectional shape of the probe relay portion 38 is formed in a plane parallel to the third perpendicular direction and the fourth perpendicular direction, but it is not limited thereto. For example, as illustrated in FIG. 9 as a first modification, and as illustrated in FIG. 10 as a second modification, the relay surface 43 may be formed in a curved shape. In the relay surface 43 with the second cross-sectional shape of the probe relay portion 38 according to the first modification, a portion more distant from the longitudinal axis according to the third perpendicular direction and the fourth perpendicular direction is located closer to the second perpendicular direction side. By contrast, in the relay surface 43 with the second cross-sectional shape of the probe relay portion 38 according to the second modification, a portion more distant from the longitudinal axis in the third perpendicular direction and the fourth perpendicular direction is located closer to the first perpendicular direction side.

As illustrated in FIG. 11 as a third modification, the relay surface 43 may be formed of a bottom plane 51 and side planes 52A and 52B. In the present modification, the side plane 52A continues between an end of the bottom plane 51 on the third perpendicular direction side and the arc curved surface 42, and the side plane 52B continues between an end of the bottom plane 51 on the fourth perpendicular direction side and the arc curved surface 42. In addition, as illustrated in FIG. 12 as a fourth modification, the relay surface 43 may be formed of inclined planes 53A and 53B. A position on the inclined plane 53A is toward the first perpendicular direction side, as the position on the inclined plane 53A is toward the third perpendicular direction side. A position on the inclined plane 53B is toward the first perpendicular direction side, as the position on the inclined plane 53B is toward the fourth perpendicular direction side.

In the first modification to the fourth modifications described above, the relay surface 43 is provided on the first perpendicular direction side with respect to the longitudinal axis C, in the second cross-sectional shape of the probe relay portion 38, like the first embodiment. With the relay surface 43 provided, the second cross-sectional shape of the probe relay portion 38 has a reduced cross-sectional area in a region on the first perpendicular direction side with respect to the longitudinal axis C, in comparison with the first cross-sectional shape of the probe main body portion 35. Thereby, in the second cross-sectional shape, the cross section gravity center Gd2 of the probe relay portion 38 is located on the second perpendicular direction side with respect to the longitudinal axis C. In addition, in the first modification to the fourth modifications described above, the second cross-sectional shape of the probe relay portion 38 is plane-symmetrical with the second reference plane P2 as the center plane, like the first embodiment. For this reason, in the second cross-sectional shape, the cross section gravity center Gd2 of the probe relay portion 38 is not shifted from the longitudinal axis C in the third perpendicular direction and the fourth perpendicular direction.

As illustrated in FIG. 13 as a fifth modification, the second cross-sectional shape of the probe relay portion 38 may be plane-asymmetrical with the second reference plane P2 as the center plane. Also in the present modification, with the relay surface 43, the second cross-sectional shape of the probe relay portion 38 has a reduced cross-sectional area in a region on the first perpendicular direction side with respect to the longitudinal axis C, in comparison with the first cross-sectional shape of the probe main body portion 35. Thereby, in the second cross-sectional shape, the cross section gravity center Gd2 of the probe relay portion 38 is located on the second perpendicular direction side with respect to the longitudinal axis C. In addition, in the present modification, the second cross-sectional shape is plane-asymmetrical with the second reference plane P2 as the center plane, but the cross section gravity center Gd2 of the probe relay portion 38 with the second cross-sectional shape is not shifted from the longitudinal axis C in the third perpendicular direction and the fourth perpendicular direction. Specifically, the second cross-sectional shape of the probe relay portion 38 is formed in a shape with which the cross section gravity center Gd2 of the probe relay portion 38 is not shifted from the longitudinal axis C according to the third perpendicular direction and the fourth perpendicular direction.

Figure 15:
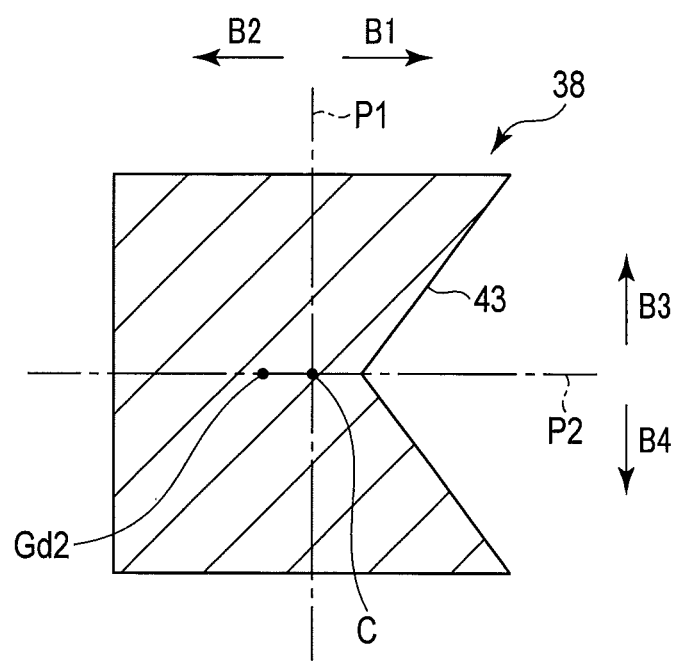
FIG. 15 is a cross-sectional view schematically illustrating a second cross-sectional shape in a cross section of the probe relay portion perpendicular to the longitudinal axis of the ultrasonic probe according to the sixth modification.

In addition, the first cross-sectional shape of the probe main body portion 35 has a circular shape in the first embodiment, but it is not limited thereto. For example, as illustrated in FIG. 14 and FIG. 15 as a sixth modification, the first cross-sectional shape of the probe main body portion 35 may be formed in a square shape with the longitudinal axis C serving as the center. Also in the present modification, the first cross-sectional shape of the probe main body portion 35 is plane-symmetrical with the first reference plane P1 serving as the center plane, and plane-symmetrical with the second reference plane P2 serving as the center plane. For this reason, in the first cross-sectional shape, the cross section gravity center Gd1 of the probe main body portion 35 is located on the longitudinal axis C.

In addition, also in the present modification, like the first embodiment, the relay surface 43 is provided on the first perpendicular direction side with respect to the longitudinal axis C in the second cross-sectional shape of the probe relay portion 38, and the second cross-sectional shape of the probe relay portion 38 has a reduced cross-sectional area in a region located on the first perpendicular direction side with respect to the longitudinal axis C, in comparison with the first cross-sectional shape of the probe main body portion 35. Thereby, in the second cross-sectional shape, the cross section gravity center Gd2 of the probe relay portion 38 is located on the second perpendicular direction side with respect to the longitudinal axis C. In addition, also in the present modification, the cross section gravity center Gd2 of the probe relay portion 38 is not shifted from the longitudinal axis C in the third perpendicular direction and the fourth perpendicular direction, like the first embodiment.

The cross-section changing portion 41 is located in the node position (most distal node position) N1 in the first embodiment, but it is not limited thereto. For example, as illustrated in FIG. 16 as a seventh modification, the cross-section changing portion 41 may be provided on the proximal direction side with respect to the node position N1. Accordingly, in the present modification, the second boundary position (boundary position) Z1 between the probe main body portion 35 and the probe relay portion 38 is provided on the proximal direction side with respect to the node position N1. However, also in the present modification, the second boundary position Z1 is located on the distal direction side with respect to the antinode position (reference antinode position) A2, like the first embodiment. As described above, the antinode position (reference antinode position) A2 is an antinode position located most distally among antinode positions located on the proximal direction side with respect to the probe curved portion 37.

With the structure described above, also in the present modification, the cross section gravity center Gd2 of the probe relay portion 38 is shifted from the longitudinal axis C only toward the second perpendicular direction, at the cross-section changing portion 41 located on the distal direction side with respect to the antinode position A2, like the first embodiment. For this reason, when the ultrasonic vibration is transmitted in the ultrasonic probe 31, the second transverse vibration is generated in a state where the first transverse vibration and the second transverse vibration cancel each other by interference. By the first transverse vibration and the second transverse vibration cancelling each other out by interference, the influence of the abnormal vibration such as the first transverse vibration and the second transverse vibration on the longitudinal vibration is reduced.

In the present modification, because the cross-section changing portion 41 is not provided in the node position (most distal node position) N1, the second transverse vibration does not have a phase opposite to the first transverse vibration. However, because the cross-section changing portion 41 is located on the distal direction side with respect to the antinode position (reference antinode position) A2, the second transverse vibration is generated in a state where the first transverse vibration and the second transverse vibration cancel each other by interference.

Stress caused by the ultrasonic vibration increases in node positions of the longitudinal vibration including the node position N1, in comparison with positions other than the node positions. In addition, stress caused by the ultrasonic vibration increases between the antinode position (reference antinode position) A2 and the proximal end of the distal treatment portion 33, as a distance from the node position N1 is small in the axis parallel direction parallel to the longitudinal axis C. The amplitude of the second transverse vibration is changed in accordance with the magnitude of stress caused by the ultrasonic vibration that acts in the cross-section changing portion 41 in which the cross section gravity center (Gd1, Gd2) is shifted in cross sections perpendicular to the longitudinal axis C. Specifically, the amplitude of the second transverse vibration increases, as the stress caused by the ultrasonic vibration acting in the cross-section changing portion 41 increases. Accordingly, the amplitude of the second transverse vibration increases, as the distance from the node position N1 to the cross-section changing portion 41 is small in the axis parallel direction.

Figure 17:
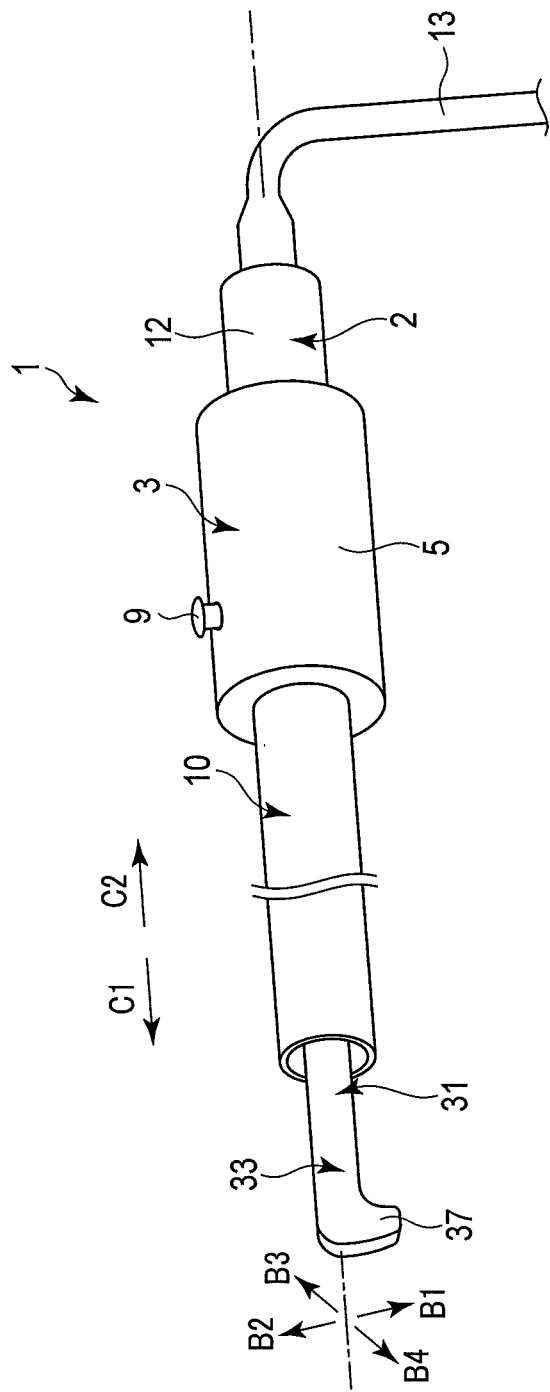
FIG. 17 is a perspective view schematically illustrating the ultrasonic treatment apparatus according to an eighth modification.

In the ultrasonic treatment apparatus 1 according to the first embodiment, the treated object held between the distal treatment portion 33 and the jaw 11 is treated using the ultrasonic vibration, but it is not limited thereto. For example, as illustrated in FIG. 17 and FIG. 18 as an eighth modification, the ultrasonic treatment apparatus 1 may not be provided with a jaw. In the ultrasonic treatment apparatus 1 according to the present modification, an ultrasonic vibration and a high-frequency current are transmitted to the distal treatment portion 33 of the ultrasonic probe 31, and the treated object is treated using the ultrasonic vibration and the high-frequency current, in a state where the distal treatment portion 33 is in contact with the treated object such as a living tissue. Also in the present modification, the energy controller 18 controls the supply state of a current to the ultrasonic transducer 21 and the supply state of a high-frequency current to the distal treatment portion 33.

Also in the present modification, the ultrasonic treatment apparatus 1 is provided with the holding unit 3, the transducer case 12, the sheath 10, and the ultrasonic probe 31, like the first embodiment. In addition, the ultrasonic transducer 21 and the horn member 23 are provided inside the transducer case 12, and an ultrasonic vibration generated by the ultrasonic transducer 21 is transmitted to the ultrasonic probe 31 via the horn member 23. The distal treatment portion 33 of the ultrasonic probe 31 is provided in a state of projecting from the distal end of the sheath 10 toward the distal direction (direction of an arrow C1 in FIG. 17). However, in the present embodiment, the holding unit 3 is not provided with the fixing handle 6, the movable handle 7, or the rotating operating knob 8. In addition, the energy operation input button 9 serving as the energy operation input section is attached to the cylindrical case 5.

Also in the present modification, the distal treatment portion 33 is provided with the probe curved portion 37, and the curved portion gravity center GB of the probe curved portion 37 is located on the first perpendicular direction side (side of a direction of an arrow B1 in FIG. 18) with respect to the longitudinal axis C. In the present embodiment, the probe curved portion 37 is formed in a hook shape (L shape). The probe relay portion 38 is continuous between the probe main body portion 35 and the distal treatment portion 33 in the axis parallel direction parallel to the longitudinal axis C. The second boundary position Z2 between the probe relay portion 38 and the probe main body portion 38 is located on the distal direction side with respect to the antinode position (reference antinode position) A2 and at a position different from antinode positions of longitudinal vibration.

The second boundary position Z2 between the probe main body portion 35 and the probe relay portion 38 is provided with the cross-section changing portion 41 that reduces the second cross-sectional area S2 of the second cross-sectional shape of the probe relay portion 38, to be smaller than the first cross-sectional area S1 of the first cross-sectional shape of the probe main body portion 35. Also in the present modification, with change from the first cross-sectional shape to the second cross-sectional shape in the cross-section changing portion 41, the cross section gravity center Gd2 in the second cross-sectional shape of the probe relay portion 38 is located on the second perpendicular direction side with respect to the longitudinal axis C, and at a position where the cross section gravity center Gd2 is not shifted from the longitudinal axis C in the third perpendicular direction and the fourth perpendicular direction, like the first embodiment. With the structure described above, the second transverse vibration is generated in a state where the first transverse vibration and the second transverse vibration cancel each other by interference.

In the embodiment and the modifications described above, the distal treatment portion (33) of the ultrasonic probe (31) includes the probe curved portion (37) that is curved from a straight state running along the longitudinal axis (C) toward the first perpendicular direction (B1) with respect to the longitudinal axis, and the curved portion gravity center (GB) of the probe curved portion (37) is located on the first perpendicular direction (B1) side with respect to the longitudinal axis (C). The probe relay portion (38) continues along the longitudinal axis (C) between the probe main body portion (35) and the distal treatment portion (33) in the axis parallel direction (C1, C2), and the boundary position (Z2) between the probe relay portion (38) and the probe main body portion (35) is located on the distal direction (C1) side with respect to the reference antinode position (A2) and at a position different from antinode positions (A1, A2) of a longitudinal vibration. The second boundary position (Z2) between the probe main body portion (35) and the probe relay portion (38) is provided with the cross-section changing portion (41) that reduces the second cross-sectional area (S2) of the second cross-sectional shape of the probe relay portion (38), to be smaller than the first cross-sectional area (S1) of the first cross-sectional shape of the probe main body portion (35). With change from the first cross-sectional shape to the second cross-sectional shape in the cross-section changing portion (41), the cross section gravity center (Gd2) in the second cross-sectional shape of the probe relay portion (38) is continuously located on the second perpendicular direction (B2) side with respect to the longitudinal axis (C).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic probe transmitting an ultrasonic vibration including a longitudinal vibration from a proximal side toward a distal side, the ultrasonic probe comprising:
a probe main body portion that has a straight longitudinal axis as a central axis, the probe main body portion extending along the longitudinal axis from a proximal end to a distal end,
a first gravity center that is located on the longitudinal axis over a first range, the first range extending from the proximal end of the probe main body portion to the distal end of the probe main body portion, the first gravity center being a gravity center of the probe main body portion in a cross-section that is perpendicular to the longitudinal axis;
a distal treatment portion provided distally of the probe main body portion,
the distal treatment portion including a probe curved portion that is curved relative to the longitudinal axis of the probe main body portion, and
the probe curved portion having a second gravity center that is spaced apart from the longitudinal axis, the second gravity center being a gravity center of the probe main body portion in a cross-section that is perpendicular to the longitudinal axis and
a probe relay portion continuously extending over a second range from the distal end of the probe main body portion to a proximal end of the distal treatment portion,
the probe relay portion including a first outer surface and a second outer surface,
wherein:
a first distance from the longitudinal axis to the second outer surface of the probe relay portion is constant over the second range,
a second distance from the longitudinal axis to the first outer surface of the probe relay portion is smaller than the first distance over the second range, the second distance being constant over the second range, and
a third gravity center, which is a gravity center of the probe relay portion in a cross-section perpendicular to the longitudinal axis, is spaced apart from the longitudinal axis over the second range.

2. The ultrasonic probe according to claim 1, wherein:
the ultrasonic probe is configured to vibrate in a predetermined vibrating state when the ultrasonic probe transmits the ultrasonic vibration, and
a reference node position, which is one of a plurality of node positions of a longitudinal vibration, is located at or near the distal end of the probe main body portion when the ultrasonic probe vibrates in the predetermined vibrating state.

3. The ultrasonic probe according to claim 2, wherein:
a first antinode position, which is one of a plurality of antinode positions of the longitudinal vibration and is separated from the reference node position towards the proximal side by a quarter of a wave length of the longitudinal vibration, is located proximally of the distal end of the probe main body portion when the ultrasonic probe vibrates in the predetermined vibrating state,
a second antinode position, which is another one of the plurality of antinode positions of the longitudinal vibration and is separated from the reference node position towards the distal side by a quarter of a wave length of the longitudinal vibration, is located distally of the proximal end of the distal treatment portion when the ultrasonic probe vibrates in the predetermined vibrating state, and
the ultrasonic probe further includes a cross-section changing portion at the distal end of the probe main body portion, a first cross-sectional area of a cross section of the probe main body portion perpendicular to the longitudinal axis being larger than a second cross-sectional area of a cross section of the probe relay portion perpendicular to the longitudinal axis due to the cross-section changing portion.

4. The ultrasonic probe according to claim 3, wherein, the third gravity center and the longitudinal axis both intersect a plane that is transverse to the longitudinal axis.

5. The ultrasonic probe according to claim 2, wherein the probe main body includes a first cross-sectional shape and the probe relay portion includes a second cross-sectional shape, the second cross-sectional shape of the probe relay portion has a reduced cross-sectional area in comparison with the first cross-sectional shape of the probe main body portion.

6. The ultrasonic probe according to claim 5, wherein, the second cross-sectional shape of the probe relay portion is symmetrical about a plane, the reference plane being perpendicular to the longitudinal axis.

7. The ultrasonic probe according to claim 3, wherein:
the reference node position is located at the cross-section changing portion when the ultrasonic probe vibrates in the predetermined vibrating state, and
the reference node position is located between the first antinode position and the proximal end of the distal treatment portion in a direction parallel to the longitudinal axis when the ultrasonic probe vibrates in the predetermined vibrating state.

8. The ultrasonic probe according to claim 7, wherein the reference node position is located most distally among the plurality of node positions of the longitudinal vibration when the ultrasonic probe vibrates in the predetermined vibrating state.

9. An ultrasonic treatment apparatus comprising:
the ultrasonic probe of claim 1; and
a vibration generator provided on the proximal side with respect to the ultrasonic probe, configured to be supplied with a current, and thereby configured to generate the ultrasonic vibration transmitted to the ultrasonic probe.

10. The ultrasonic treatment apparatus according to claim 9, further comprising an energy controller configured to control a supply state of the current generating the ultrasonic vibration to the vibration generator, and configured to control a supply state of a high-frequency current to the distal treatment portion.

11. The ultrasonic treatment apparatus according to claim 9, further comprising a jaw openable and closable relative to the distal treatment portion of the ultrasonic probe.

12. The ultrasonic treatment apparatus according to claim 11, further comprising an energy controller configured to control a supply state of the current generating the ultrasonic vibration to the vibration generator, and configured to control a supply state of a high-frequency current to the distal treatment portion and the jaw.

* * * * *